United States Patent
Moses et al.

(10) Patent No.: US 7,297,963 B2
(45) Date of Patent: Nov. 20, 2007

(54) METHOD FOR DETERMINATION OF FUEL THERMAL STABILITY

(75) Inventors: Clifford A. Moses, New Braunfels, TX (US); David W. Naegeli, San Antonio, TX (US); George R. Wilson, III, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 11/415,860

(22) Filed: May 2, 2006

(65) Prior Publication Data

US 2006/0263893 A1    Nov. 23, 2006

Related U.S. Application Data

(60) Provisional application No. 60/676,881, filed on May 2, 2005.

(51) Int. Cl.
*G01N 21/64* (2006.01)
(52) U.S. Cl. ................ 250/459.1; 250/458.1; 356/318
(58) Field of Classification Search ............ 250/458.1, 250/459.1; 356/318
See application file for complete search history.

(56) References Cited

U.S. PATENT DOCUMENTS 5,198,871 A * 3/1993 Hill et al. .................. 356/318
5,223,718 A * 6/1993 Taboada ................... 250/458.1
5,424,959 A * 6/1995 Reyes et al. ................ 702/28
5,468,262 A * 11/1995 Acker et al. ................ 44/348
5,472,878 A * 12/1995 Lewis et al. ................ 436/61

OTHER PUBLICATIONS

Naegeli, David W., "Thermal Stability of Jet Fuels: Kinetics of Forming Deposit Precursors." Final Report for NASA Contract No. NAG 3-1739, NASA Technical Reports [online], Jun. 1997 [retrieved on Nov. 14, 2006]. Retrieved from the Internet: <URL: http://ntrs.nasa.gov/archive/nasa/casi.ntrs.nasa.gov/19970025575_1997040925.pdf>.*

* cited by examiner

*Primary Examiner*—David Porta
*Assistant Examiner*—Mark R Gaworecki
(74) *Attorney, Agent, or Firm*—Grossman, Tucker, et al (57) ABSTRACT

A method of evaluating thermal stability of a fuel and an apparatus used therein. The method includes heating the fuel to a given temperature, directing light through the heated fuel a first time wherein the light is of an intensity and of a wavelength to induce fluorescence and obtaining a first fluorescence data, directing the light through the fuel at least a second time that is later in time and obtaining a second fluorescence data, and measuring any changes to fluorescence from the heated fuel over time.

13 Claims, 5 Drawing Sheets

METHOD FOR DETERMINATION OF FUEL THERMAL STABILITY

This application claims priority to U.S. Provisional Application Ser. No. 60/676,881, filed May 2, 2005, incorporated herein in its entirety by reference.

FIELD OF INVENTION

This invention relates to an apparatus and method for determining the thermal stability of a fuel such as aviation fuel using light induced fluorescence.

BACKGROUND OF THE INVENTION

The relative thermal stability of jet fuel is an important factor in practice. The standard test for this property, the JFTOT method (ASTM D3241), is used as a qualitative test to determine whether the fuel can be used. This test method covers the procedure for rating the tendencies of gas turbine fuels to deposit decomposition products within the fuel system. The fuel is tested at a required minimum temperature to determine if it meets minimum acceptance criteria. The JFTOT test basically determines whether the fuel passes or fails the test based on the breakpoint of the fuel. The breakpoint method requires running multiple JFTOT tests with an equivalent multiplication of time. The test usually takes about three hours. The breakpoint of the fuel is defined as the highest temperature in degrees Centigrade at which the fuel receives a passing rating. For example, the minimum JFTOT breakpoint for salable jet fuel is 260 degrees Centigrade.

While the JFTOT has proven successful in ensuring the delivery of quality jet fuel, there has always been a desire for a quicker screening test especially for storage and transportation monitoring. If there is a suspicion of a problem, the JFTOT is employed but it takes too much time for routine analysis. A quick, routine screening tool could eliminate needless testing on otherwise good fuel and ensure testing of potentially bad fuels that would have been overlooked.

U.S. Pat. No. 5,198,871 discloses the use of laser induced fluorescence (LIF) to measure the presence of heavy molecules (deposition precursors) and evaluate the quality of fuels. In U.S. Pat. No. 5,198,871, a sample is illuminated to cause it to produce fluorescent radiation. The spectral representation of the fluorescence produced by the sample is compared to a reference spectrum to obtain an indication of the physical characteristics of the sample based on the supposition that the fluorescence is proportional to the amount of the precursor present in the sample for a given fuel.

However, U.S. Pat. No. 5,198,871 provided no correlation between the fluorescence and the thermal stability. Furthermore, fuels may naturally fluoresce, some more than others. Moreover, past researchers have attempted to describe the chemistry of deposition with limited success. Specifically, the past researchers developed models that were not universally applicable.

SUMMARY OF THE INVENTION

The present inventors have recognized that a need exists for a solution to one or more of the deficiencies discussed above.

In one broad respect, the present invention is a method of evaluating thermal stability of a fuel, comprising heating the fuel to a given temperature, directing light through the heated fuel a first time wherein the light is of an intensity and of a wavelength to induce fluorescence of the fuel and obtaining a first fluorescence data, directing the light through the fuel at least a second time that is later in time and obtaining a second fluorescence data, and measuring any changes to fluorescence from the heated fuel over time. The fuel sample is thus illuminated with the light from the energy source and the fluorescence observed and measured. The data from the at least two illumination times will provide a plot of fluorescence versus time which can be compared with a database of plots at given breakpoints for a given fuel to determine whether the fuel should be, for example, further tested with the JFTOT method. The method of this invention allows both qualitative and quantitative evaluation of the fuel.

In another broad respect, the present invention is a system for evaluating the thermal stability of a fuel, comprising: at least one heater, at least one energy source, at least one fuel sample container, at least one fluorescence detector that provides output data, and at least one computational device that analyzes the output data signal.

In another broad respect, this invention is a method for manufacturing a system for evaluating the thermal stability of a fuel, comprising: providing at least one heater, providing at least one energy source, providing at least one fuel sample container, providing at least one fluorescence detector that provides output data, and providing at least one computational device that analyzes the output data signal.

This invention provides a relatively quick, routine screening tool that can eliminate needless testing using JFTOT on otherwise good fuel and ensure testing of potentially bad fuels that would have been overlooked.

DETAILED DESCRIPTION OF THE INVENTION

A basic system that may be employed in the practice of this invention is shown in U.S. Pat. No. 5,198,871, incorporated herein by reference. The system shown in U.S. Pat. No. 5,198,871 lacks, however, a heater within the system that is used to heat samples to a given temperature in the practice of this invention. The present inventors have recognized the advantages of heating the fuel samples prior to or concurrent with directing light of an appropriate wavelength and intensity at the fuel.

Figure 1:
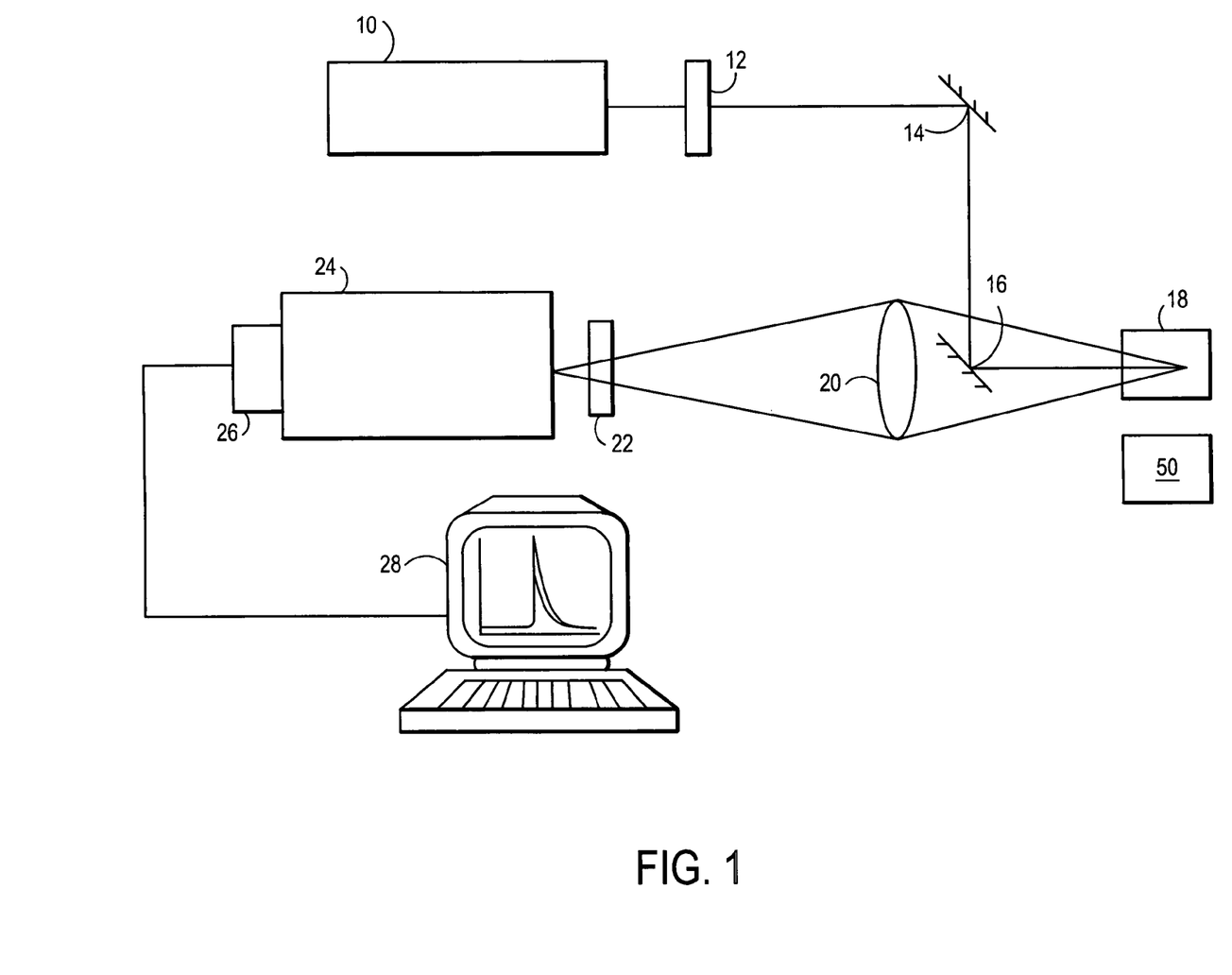
FIG. 1 shows a representative system according to this invention.

A system that can be used in the practice of this invention is depicted in FIG. 1. In FIG. 1, light from an excitation source 10 is passed through a filter 12 and reflected by mirrors 14 and 16 to illuminate a fuel sample 18 to be tested for fluorescence. In one embodiment, the energy source 10 is a laser having a suitable wavelength to cause fluorescence. The energy source can be blue light in the wavelength range of 440-500 nanometers (nm), such as from the 488 nm line of an Argon gas laser. Laser sources, gas or solid state, in the stated range can also be used. Lasers are relatively easy to use in this application because of the relative strength of their coherent source and monochromicity. A monochromator may be used if a broadband light source is employed, such broad band sources including a xenon bulb commonly used in UV/VIS systems. The intensity of the light induced fluorescence is measured and the monochromator is set at the wavelength of peak fluorescence intensity. Other light sources can be used if sufficient light can be brought to bear on the sample. One example of such other light sources is blue diodes. Another example would be blue light separated from a broad-spectrum source by diffraction or filtration.

The fluorescence characteristics of the test sample 18 are determined by analysis of the light fluorescence by the fuel sample. The fluoresced light passes through lens 20 and filter 22, and is used as input for the fluorescence detector 24. The filter 22 can be selected to minimize the scattered light from the laser 10. The resultant fluorescence from the fuel sample is measured by a fluorescence detector 24 that can provide an output data signal. A representative example of a fluorescence detector is a spectrometer. If the fluorescence detector 24 is a spectrometer, the spectrometer disperses the light which is then detected by the diode array detector 26 and amplified to provide input for a suitable display device 28, such as a computer display 28 shown in FIG. 1. This provides an opportunity to evaluate the nature of the fluorescence in addition to providing a total amount of fluorescence. In practice, for a qualitative test, a simple totalizer may be sufficient. This could be accomplished by focusing the total fluorescence into a photomultiplier tube (PMT) or equivalent device. The PMT responds to all the light hitting the detector and provides a single output.

The fuel sample can be held in a suitable container in a position that allows the light to enter and exit the fuel sample without distorting the light. For example, the container can be made of quartz or glass such as in the form of an ampoule or cell, which can be removable or permanently stationed in a position to receive the light. The volume of the container, and the amount of sample used, can vary widely. The amount of fuel sample should be at least the minimum required to perform the fluorescence testing described herein.

The container with the fuel sample is placed on or in a heater 50 so that the fuel can be heated and/or maintained at a given temperature on the apparatus. The heater in one embodiment includes a temperature gauge, such as a thermocouple, to detect the temperature of the fuel. The heater can also include appropriate functionality to allow automatic detection and adjustment of the temperature. In one embodiment, the heater supplies heat to the fuel sample in the container as the container is irradiated with the light. Alternatively, the heater is separate from the laser system. In this case the sample is heated for a given period of time at a given temperature then either irradiated immediately or cooled to stop further formation of deposition precursors.

While not wishing to be bound by theory, it is believed that deposition precursors fluoresce once they reach a certain size, such as when the molecules form oligomers. Fuel "gum" is believed to be made up of the deposition precursors after they accumulate and precipitate from solution. Varnishes and lacquers may also build up in the fuel. The gum can be peroxides, peroxide decomposition products, and other oxygenated products such as alkylperoxyl compounds and may contain other heteroatoms such as sulfur and nitrogen. It is believed that the gums are the precursors to deposit formation. It is believed that thermal stability of a fuel corresponds to the fuel's tendency to form gums. It should be appreciated that the particular type of fuel being tested can influence the fluorescence of the precursors. For example, a given amount of a particular precursor in a first fuel may fluoresce as much as twice the amount of the same precursor in a second fuel. In addition, it is believed that the heavy materials measured in accordance with this invention are the precursors of the deposition that is measured by the JFTOT test. It should also be noted that a fuel's thermal stability is a fuel property, with a given thermal stability corresponding to a given resistance to the formation of deposition precursors.

If one uses the method described in U.S. Pat. No. 5,198,871 to measure light induced fluorescence of a series of fuels, one finds a general relationship between the measured fluorescence and the jet fuel breakpoint temperature. The present inventors have recognized that there are, however, notable exceptions (outlying data points) that often occur, such as high fluorescence, good stability fuel and low fluorescence, poor stability fuel. The present inventors have found that heating the fuel samples and measuring the resultant change in light induced fluorescence can resolve these problems.

Figure 2:
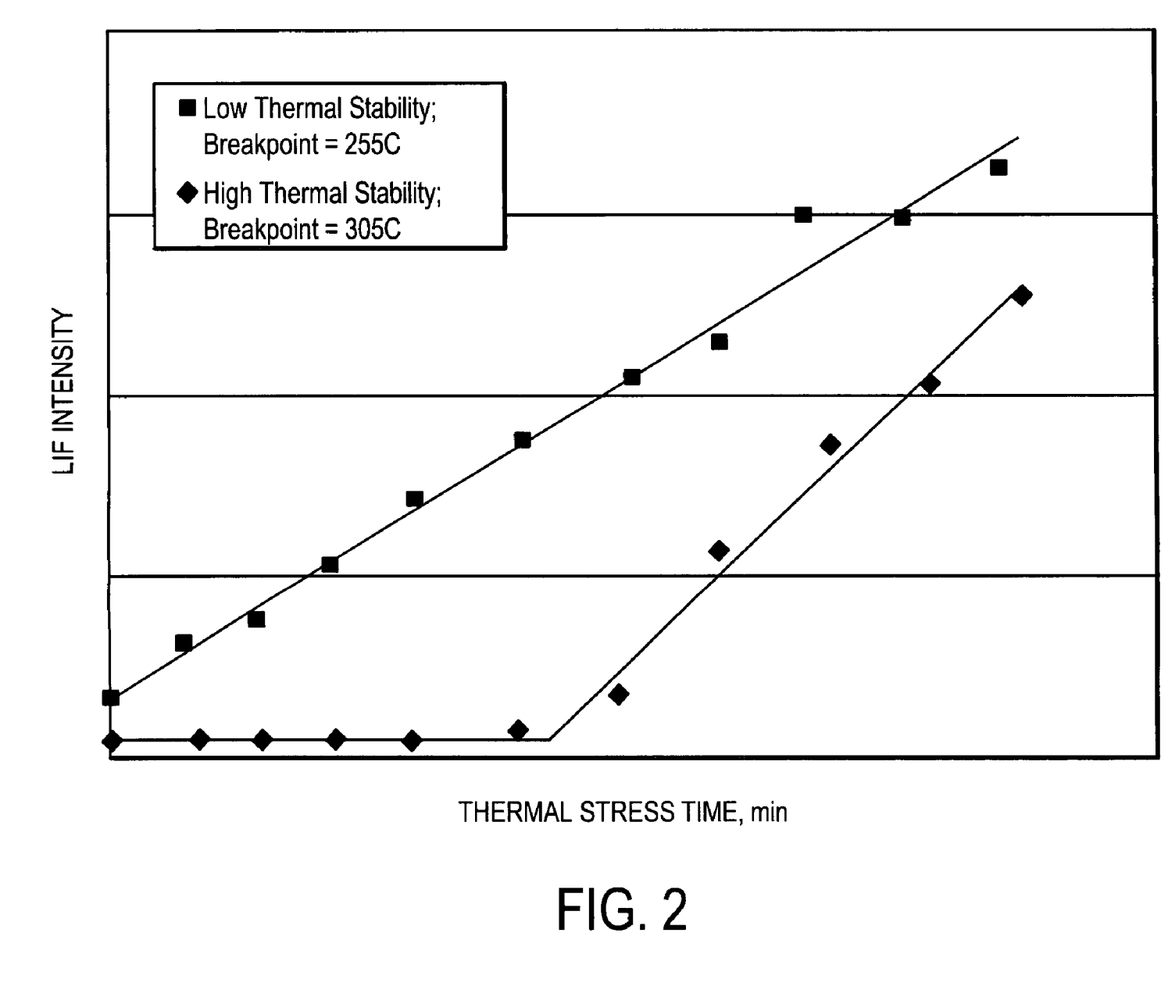
FIG. 2 shows a plot of light induced fluorescence (LIF) intensity versus thermal stress time for two fuels.
Figure 3:
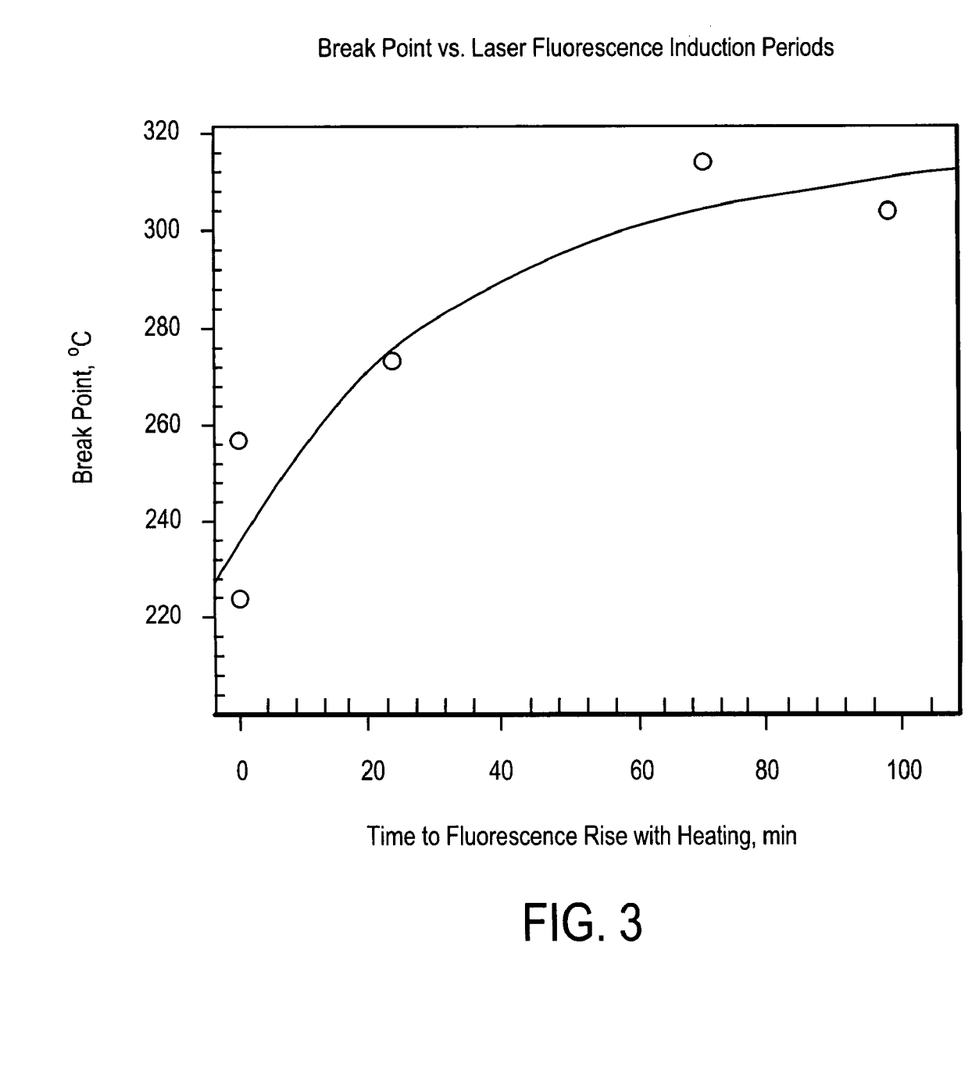
FIG. 3 shows a plot of breakpoint (in degrees Centigrade) versus the time to fluorescence rise with heating of a fuel sample.

Thus, a sample is heated at a given temperature, held at that temperature for a given period of time, with light induced fluorescence data being periodically taken. Based on light induced fluorescence data obtained, one can determine a rate of light induced fluorescence change. The factors that can influence the results include but are not limited to the time before significant light induced fluorescence change (induction time) and the rate of light induced fluorescence change (formation rate of the precursors). This is shown in FIG. 2, which a plot of light induced fluorescence versus thermal stress time for two different fuels. In the fuel with the high thermal stability with a breakpoint of 305 degrees Centigrade, there is an induction time before onset of precursor fluorescence. The fuel with the lower thermal stability shows light induced fluorescence sooner in time. For both fuels in FIG. 2, the formation rate of the precursors can be determined by determining the slope of the data points. All of this data can be used to help discriminate the quality of fuels, alone and in combination. In this regard, FIG. 3 is a plot of breakpoint versus induction periods. That is, jet fuel breakpoint is compared to time to fluorescence rise with heating in minutes.

In the practice of this invention, in general, a fuel sample from a given fuel to be tested is placed in the container. Laser light of an appropriate wavelength is directed at the sample for a given period of time and fluorescence is detected and analyzed by the spectrometer, with data from the spectrometer being sent to the computer where the data is further analyzed for fluorescence using appropriate software. At each temperature for a given sample, a plot of fluorescence versus time is generated. Next, the fuel sample (or a new fuel sample) is next heated to a higher temperature (e.g., at a temperature 10 degrees Centigrade higher) and the light induced fluorescence procedure repeated, with a new plot of data points obtained at the new temperature. These steps are repeated until a desired number of plots of fluorescence versus time are obtained. It should be noted that as an alternative to the device of this invention including a heating unit which may be used to heat the sample, the samples can be heated separately and optionally cooled to stop further chemical reaction. For example a number of samples can be heated together and each sample is cooled after a different period of heating so that the set of samples includes individual fuel samples that have been heated varying periods of time, with the sample that is heated the longest typically having the largest amount of deposition precursors and highest fluorescence of this batch of samples.

Thus, static samples can be employed to effect more rapid evaluation. The evaluation may be made with a single sample or with two samples, one being a base reference. The fluorescence may be measured after the heating is completed or it may be measured concurrently with heating. If concurrently measured the heating may be kept static or ramped from lower to higher temperatures. In addition, in the practice of this invention flowing samples may be used in an isothermal system. In this configuration, in one embodiment, the fuel's light induced fluorescence will be measured before entering an isothermal flow loop and then again after exiting. The temperature of the flow loop may be ramped in a manner to maintain an isothermal or semi-isothermal flow. Flowing samples may be used in non-isothermal systems such as JFTOT. This could include both laminar and turbulent flow systems. For example the method and apparatus of this invention might be added to the JFTOT device to provide an objective evaluation of fuel performance in lieu of the current subjective evaluation technique.

Each plot of fluorescence at a given temperature will define a line or curve. As might be expected, the fluorescence increases with increasing temperature. That is, the slope of the curves increases as temperature increases.

Next, the slopes of the plots at given temperatures are derived and themselves plotted against temperature to provide a line with a given slope. It has been found that a given fuel will have a distinctive plot of slope versus time. Once the characteristics of a given fuel at a variety of predetermined breakpoints have been measured, a database of plots can be created for this fuel. When a given fuel is to be tested, the type of fuel will provide an appropriate plot on which the light induced fluorescence data for the fuel to be tested can be compared in order to determine whether the fuel to be subjected to the further testing or, alternatively, whether the fuel to be tested is acceptable for use as aircraft fuel.

It is anticipated that this invention could be used in two major formats. First, the invention can be in the form of a laboratory instrument where the sample is brought to the machine. This format might be as a portable tester for field analysis to a sophisticated bench-top analysis system. The second format would be as an online analyzer where the sample is supplied on a continuous basis from a process or pipeline, which could provide real-time measurements to assess, for example, whether a JFTOT is required.

Figure 4:
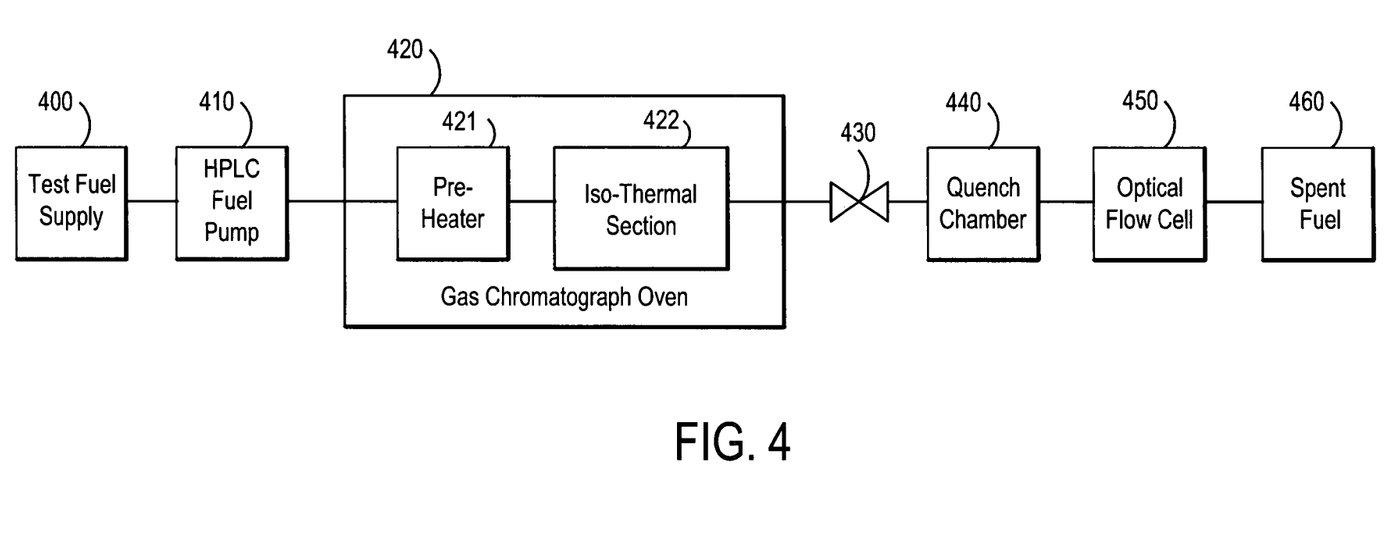
FIG. 4 shows a flow chart scheme that is representative of the process of this invention.

A portion of a system that may be employed in the practice of this invention is depicted in FIG. 4. In FIG. 4, a test fuel sample 400 that is saturated with oxygen is pumped via pump 410, such as a high performance liquid chromatography pump, to an oven 420, such as a gas chromatograph oven, wherein the sample is exposed to an isothermal process using, for example, a preheater 421 and an isothermal section 422. In the oven 420 the sample is exposed to variable temperature and time combinations in accordance with this invention. After passing through the oven 420, the fuel is pumped through open valve 430 to quench chamber 440 and then to the optical flow (LIF) cell 450 where fluorescence is measured. The fuel exits optical flow cell 450 as spent fuel 460. This system provides a relation between generated fluorescence and predicted fuel composition. It should be appreciated that the fluorescence may be measured after the heating is completed or may be measured concurrently. If fluorescence is measured concurrently, the heating may be ramped from lower to higher temperatures. The invention can be practiced using static samples or with flowing samples. The fuel LIF can be measured before entering the isothermal flow loop depicted in FIG. 4 and then again after exiting. The temperature of the flow loop may be ramped in a manner to maintain a semi-isothermal flow. Also, this invention can be practiced with flowing samples in a non-isothermal systems such as the JFTOT. This could include both laminar and turbulent flow systems. For example, this technique might be added to the JFTOT device to provide an objective evaluation of fuel performance in lieu of the current subjective evaluation technique. The temperatures can again be ramped.

Figure 5:
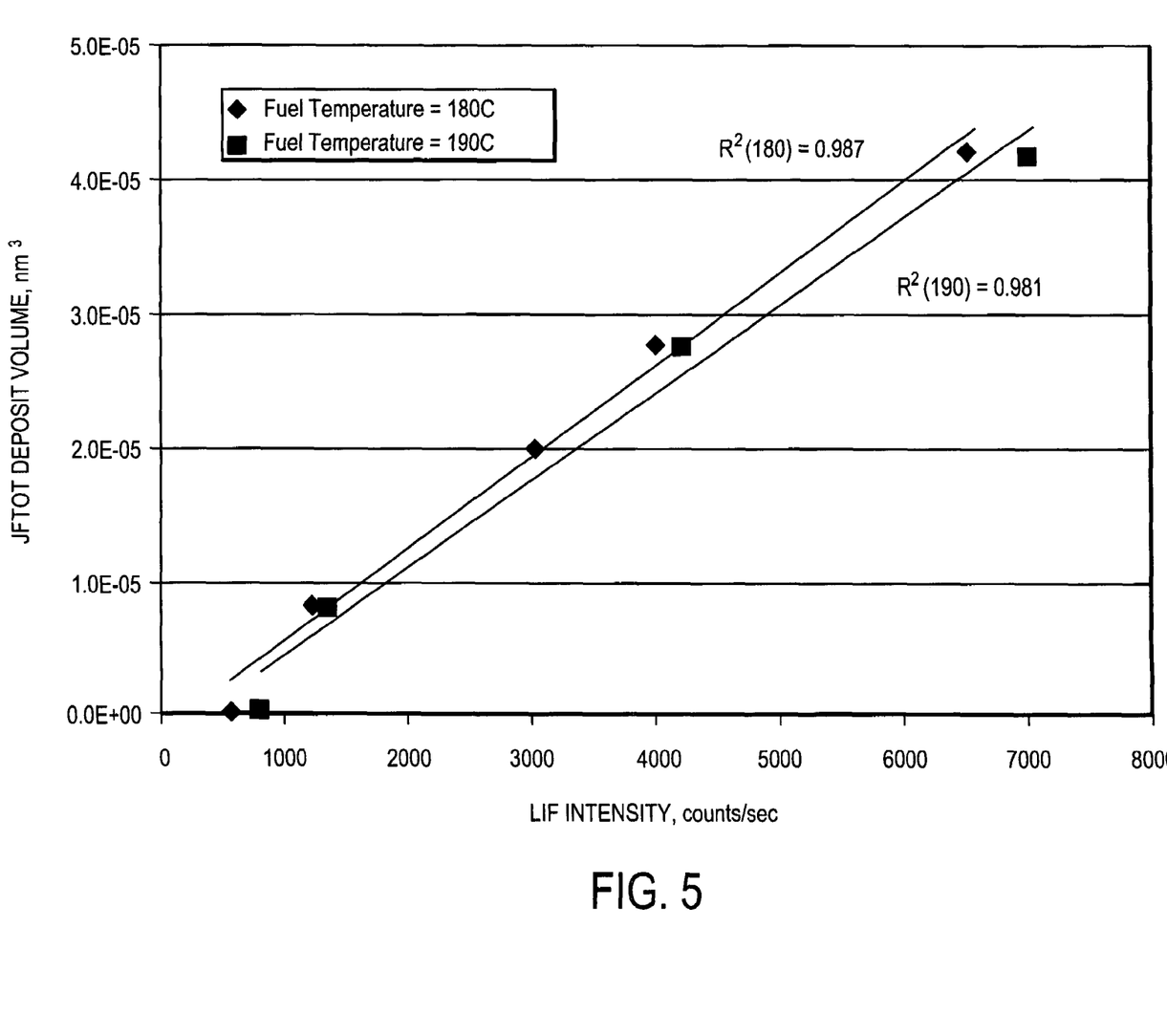
FIG. 5 shows a representative plot of JFTOT deposit volume ($nm^3$) versus LIF intensity (counts per second)

Using the system depicted in FIG. 4, the data points and graphs depicted in FIG. 5 was generated. Thus in FIG. 5, the LIF output from the system is compared to the isothermal setpoints listed in the graph. Isothermal temperatures of 180 C. and 190 C. were employed. The projected value was obtained by generating an Arrenhius plot (deposit volume vs. 1/K) from the breakpoint data from five fuels in the test and then finding the calculated deposit volume at 1/K=1.8 for each fuel. Thus the LIF generated in the isothermal oven was compared to the amount of expected deposit in a JFTOT at a fixed temperature, assuming there were no second or higher reaction kinetics involved at higher temperatures.

In addition, it has been found by the present inventors that the presence of fluorescence alone is not necessarily the only factor in determining the thermal stability of a fuel. While not wishing to be bound by theory, the inventors posit the following general model for fuel stability: $B=a+f(I)-f(R)$, wherein B is the breakpoint, a is the nominal fuel stability, $f(I)$ is the inhibition factor which increases stability, and $f(R)$ is the reaction factor which reduces stability. Based on the refined nature of fuels such as jet fuel, it can be assumed that there is an inherent level of staility (i.e., "a"). Stability is enhanced by factors that inhibit the formation of deposition precursors, which might be the result of the lack of reactant material or the presence of antioxidants, natural or added, but the effects are the same. This can be referred to as $f(I)$. Stability is degraded by factors that promote the formation of deposit precursors. This can be the increased presence of reactive materials or catalytic agents but the effect is the same. This can be referred to as $f(R)$. This concept can be measured by the appearance and increase in fluorescence. Thermal stability is an oxidative property so the measurement of the oxidation process is an important component, but both place a part in the determination of the primary factors. The method disclosed herein, including the method shown in FIG. 4 can be used to make this determination.

The following examples are representative and not intended to limit the scope of this invention or the claims hereto.

Eleven 4 mL aliquots of jet fuel are sealed in standard ampoules. Ten of these ampoules are placed in a heated block held at constant temperature (typically 160 degrees Centigrade but it can vary between 100 and 220 degrees Centigrade). Periodically, the sample ampoules are removed from the heated block and quenched by water immersion to stop the chemical reactions. After the heating is completed the samples, including the unheated base sample, are measured for light induced fluorescence. An argon laser emitting about 30 mw at 488 nm and a 0.64 meter Czerny-Turner mounted monochromator to measure the fluorescence in the 500 nm to 700 nm region of the spectrum are employed. While the fluorescence spectra of different types of aviation fuels are often very similar, they exhibit slight variations in signature. The characteristic most pertinent to the light induced fluorescence measurement is the wavelength at peak fluorescence intensity. Since it typically varies from 518 nm to 548 nm, a scan of the fluorescence spectrum is required to determine the wavelength at peak fluorescence intensity. The light induced fluorescence intensity is measured setting the monochromator at the wavelength of peak fluorescence intensity. The resultant fluorescence is measured by spectrometer. These measurements are then used to evaluate the thermal stability of the fuel in a computer equipped with appropriate software.

Although illustrative embodiments and methods have been shown and described, a wide range of modifications, changes, and substitutions is contemplated in the foregoing disclosure and in some instances some features of the embodiments or steps of the method may be employed without a corresponding use of other features or steps. Accordingly, it is appropriate that the claims be construed broadly and in a manner consistent with the scope of the embodiments disclosed herein.

What is claimed is:

1. A method for evaluating a sample of fuel comprising:
    providing a database of fluorescence data for at least one fuel, wherein said database comprises at least one of a first set of fluorescence versus time at a plurality of different temperatures and a first set of a rate of light induced fluorescene change versus time at a plurality of different temperatures;
    generating sample data for a sample of fuel, said sample data comprising at least one of a second set of fluorescence versus time at a plurality of different temperatures and a second set of rate light induced fluorescence change versus time at a plurality of different temperatures;
    comparing said sample data and said database of fluorescence data; and
    determining whether said sample of fuel is to be subject to further testing or whether said sample of fuel has an acceptable thermal stability based on said comparing of said sample data and said database data.

2. The method of claim 1 wherein said database of fluorescence data comprises fluorescence data at temperatures in the range of about 100 to about 200 degrees Centigrade.

3. The method of claim 1 wherein generating sample fluorescence data for a sample of fuel comprises fluorescence data at temperature in the range of about 100 to about 200 degrees Centigrade.

4. The method of claim 1 wherein the fluorescence data for said at least one fuel is generated by passing light through said fuel wherein said light has a wavelength in the range from 440 to 500 nanometers.

5. The method of claim 1, wherein said fluorescence data for said sample of fuel is generated by passing light through said fuel wherein said light has a wavelength in the range from 440 to 500 nanometers.

6. The method of claim 1 wherein said fluorescence versus time at a plurality of different temperatures for said at least one fuel has a wavelength of 500 to 700 nanometers.

7. The method of claim 1 wherein said fluorescence versus time at a plurality of different temperatures for said sample of fuel has a wavelength of 500 to 700 nanometers.

8. The method of claim 1 wherein said fluorescence data for said at least one fuel at a plurality of different temperatures comprises temperatures that differ by 10 degrees Centigrade.

9. The method of claim 1 wherein said fluorescence data for said sample of fuel at a plurality of different temperatures that differ by 10 degrees Centigrade.

10. The method of claim 1 wherein said database of fluorescence data for said at least one fuel is generated with a laser.

11. The method of claim 1 wherein said sample fluorescence data is generated with a laser.

12. The method of claim 1 wherein said at least one fuel or said sample of fuel comprises a jet fuel.

13. A method of evaluating a sample of fuel, comprising:
    providing a database of fluorescence data for at least one fuel, wherein said database comprises at least one of a first set of fluorescence versus time at a plurality of different temperatures and a first set of rate of light induced fluorescence change time at a plurality of different temperatures;
    generating fluorescences data for a sample of fuel comprising exposing said sample to light and measuring fluorescence versus time at a first and a second temperature wherein said second temperature is different than said first temperature;
    determining a first and a second rate of light induced fluorescence change versus time for said sample as a function of temperature at said first and said second temperatures;
    comparing said fuel fluorescence data and said sample fluorescence data; and
    determining whether said sample of fuel is to be subject to further testing or whether said sample of fuel has an acceptable thermal stability based on said comparing of said fuel fluorescence data and said sample fluorescence data.

* * * * *

UNITED STATES PATENT AND TRADEMARK OFFICE
CERTIFICATE OF CORRECTION

PATENT NO. : 7,297,963 B2  Page 1 of 1
APPLICATION NO. : 11/415860
DATED : November 20, 2007
INVENTOR(S) : Moses et al.

It is certified that error appears in the above-identified patent and that said Letters Patent is hereby corrected as shown below:

In column 7, line 23, in Claim 1, delete "a" before "rate".

In column 7, line 24, in Claim 1, delete "fluorescene" and insert -- fluorescence --, therefor.

In column 7, line 29, in Claim 1, after "rate" insert -- of --.

In column 7, line 44, in Claim 3, delete "temperature" and insert -- temperatures --, therefor.

In column 8, line 16, in Claim 9, after "temperatures" insert -- comprises temperatures --.

In column 8, line 24, in Claim 12, delete "comprises" and insert -- comprise --, therefor.

In column 8, line 30, in Claim 13, after "change" insert -- versus --.

In column 8, line 32, in Claim 13, delete "fluorescences" and insert -- fluorescence --, therefor.

Signed and Sealed this

Twenty-ninth Day of July, 2008

JON W. DUDAS
*Director of the United States Patent and Trademark Office*